United States Patent [19]

Murphy

[11] Patent Number: 4,506,393
[45] Date of Patent: Mar. 26, 1985

[54] METHOD OF PROSTHESIS DESIGN

[76] Inventor: Stephen B. Murphy, 10 Dartmouth St., Winchester, Mass. 01890

[21] Appl. No.: 480,007

[22] Filed: Mar. 29, 1983

[51] Int. Cl.³ .............................................. A61F 1/00
[52] U.S. Cl. ................................................. 3/1; 3/1.9; 128/92 C; 128/653; 264/138
[58] Field of Search .................... 128/1 R, 92 R, 92 C, 128/92 E, 92 EB, 635; 3/1, 1.9, 1.91, 1.911, 1.912, 1.913; 364/414, 571

[56] References Cited

U.S. PATENT DOCUMENTS

| | | | |
|---|---|---|---|
| 4,144,578 | 3/1979 | Mueller et al. | 364/571 |
| 4,275,444 | 6/1981 | Ryan | 364/414 |
| 4,294,544 | 11/1981 | Altschuler et al. | 356/376 |
| 4,326,252 | 4/1982 | Kohmo et al. | 364/414 |
| 4,436,684 | 3/1984 | White | 128/653 X |

FOREIGN PATENT DOCUMENTS 3001521  4/1981  Fed. Rep. of Germany ........... 3/1.9

OTHER PUBLICATIONS

Roberts "Design of a Continuous Fiber Composite Surface Hip Replace", vol. 102, Journal of Mechanical Design; pp. 688–694; 1980.

Primary Examiner—Richard J. Apley
Assistant Examiner—David J. Isabella

[57] ABSTRACT

A prosthesis is fitted to a body structure into which it is to be inserted by establishing an initial prosthesis shape and thereafter withdrawing the shape from the body structure in a sequence of defined increments and determining, for each increment, the minimum volume to be removed from the prosthesis to avoid interference with the body structure.

13 Claims, 6 Drawing Figures

METHOD OF PROSTHESIS DESIGN

BACKGROUND OF THE INVENTION

1. Field of the Invention

The invention relates to prostheses and, more particularly, to a method of forming a prosthesis for fit to a specific body section.

2. Prior Art

Prostheses replace injured or destroyed body portions, and have become increasingly common, as well as complex. Although a certain amount of individual fitting is always required, prostheses typically accomodate a limited range of sizes, and the "fitting" process has generally focused on determining the largest standard prosthesis that is easily accomodated by the body section and creating an interface between the prosthesis and the body portion with which it is to work so as to accomodate the two. The interface is frequently subjected to high stresses, and commonly is a cause of discomfort and even malfunction.

The steady increase in available computer computational power has significantly improved prosthesis design. However, the improvement has largely been focused on creating universal designs which must then be interfaced to the selected body parts. The desirability of a user-specific (i.e., "customized") prosthesis has been recognized, but the difficulties in achieving this goal are considerable. Operations involving manual fitting, such as by using templates of the parts to be fitted and appropriately adjusting the templates, are laborious, subject to operator error, and not consistently repeatable in results. Fully automated processes would, therefore, be preferable, but the calculations involved for a prosthesis and body structure of any complexity are considerable, and may render the cost prohibitive.

OBJECTS OF THE INVENTION

Accordingly, it is an object of the invention to provide an improved method of prosthesis design.

Further, it is an object of the invention to provide a method of prosthesis design which significantly reduces the computations required for the design.

Further, it is an object of the invention to provide a method of designing a user-specific prosthesis which is comparatively inexpensive to implement and which results in a more closely-fitting, strengthened prosthesis.

Still another object of the invention is to provide an improved prosthesis that provides a superior fit to the user as compared to a standard prosthesis.

BRIEF SUMMARY OF THE INVENTION

In accordance with the present invention, a trial prosthesis is generated from a contour of a body part to which the prosthesis is to be fitted. For purposes of explanation, the invention will be described in connection with the implementation of a total hip prosthesis, but it should be understood that the invention is more broadly applicable. Accordingly, the specific illustrations will be given in terms of lateral and medial locations, as well as proximal and distal locations, all as commonly used in reference to a hip and femur.

The body contour of interest in applying the present method to design of a hip replacement prosthesis is the femoral canal, and the canal contour is preferably generated by scanning the body portion to which the prosthesis is to be fitted and forming an "image" from the scan. Recently developed techniques such as Computer Aided Tomography are particularly useful in obtaining such a scan. Such scans typically form a two-dimensional image, and a multiplicity of such scans may then be used to form a three-dimensional image. As used here, the term "image" includes a visually-observable image, but is not so limited. For example, the "image" may exist solely in the form of stored data in a computer.

In carrying out the invention, a "trial" prosthesis image is initially formed to conform to the contour of the body section to which the prosthesis is to be fitted. The initial prosthesis "image" is generated with little or no regard for the need for insertion or removal of the prosthesis. These matters are then addressed in the prosthesis design as follows:

A plurality of longitudinally-spaced cross-sections of the canal are first determined. These cross-sections are preferably spaced apart by an amount that is of the order of from 1% to 5% of the prosthesis length. This spacing provides a reasonably smooth contour for the prosthesis while not unduly increasing the required computation. The centroids of these cross-sections are then determined, and a reference point for each of the cross sections is now derived from the cross sections and the centroids.

In particular, if the respective cross sections were viewed as projected onto a common plane, it would be seen that a line connecting the centroids of a plurality of adjacent cross sections (e.g., the two immediately above and below) a given cross section, as well as the centroid of the cross section itself, intersects the given cross section at two separate points. One of these intersections is chosen as the reference point for the given cross section. These reference points effectively establish a path along which predetermined portions of the prosthesis are to move during withdrawal. (In the case of a hip prosthesis, the preferred reference points are in the general lateral direction on the lower portion of the prosthesis, and in the general medial direction on the upper portion of the prosthesis. The distal tip of the prothesis will then follow the path defined by the lower lateral intersections, while the proximal portion of the prosthesis will move along the path defined by the upper medial intersections.) This serves to improve the fit of the prosthesis to the canal in the regions of the reference points and thus in those areas where body stresses are high. Similarly, it diminishes the volumes removed in these regions and thus further enhances the prosthesis-canal interface.

The prosthesis image is then moved longitudinally outwardly with respect to the canal image by a finite increment. The base cross-section of the prosthesis may be moved to a position coincident with the next higher canal cross-section or it may be moved to a defined position intermediate two adjacent canal cross-sections. The latter position requires interpolation of the canal reference points in performing the operations described herein and thus slightly increases the required computation, but allows a smoother fit for a given number of canal cross-sections. Thereafter, the centroid of the bottom cross-section of the prosthesis (hereinafter referred to as the "base" prosthesis centroid) is translated toward the canal reference point (or the interpolated canal reference point) at that level, preferably along a line joining the canal centroid and canal reference point, until the prosthesis cross-section intersects the canal reference point at that level. The intersection is hereinafter referred to as the "distal tip intersection" at the given level. This fixes the location of the distal tip for the subsequent operations at the given level. The spatial orientation of the prosthesis is next fixed as now described.

A proximal canal uppermost reference point ("exit point") is then established, preferably in the region of the calcar femorale. As was previously the case with the distal canal reference point, the exit point may be selected directly by the clinician or may be determined by the method provided herein, that is, as the intersection of the planar projection of the centroidal canal line with the canal cross-sections at the proximal end of the canal. The centroid of the prosthesis in the plane coincident with this canal cross-section is also determined and the prosthesis centroid rotated about the distal tip intersection and toward the proximal canal reference point until intersection occurs between the prosthesis image and canal image. This fixes the initial spatial orientation of the prosthesis for the given level.

The position and orientation of the prosthesis as so far defined would be at, or near, the optimal position for insertion or removal of the prosthesis (that is, the position and orientation yielding maximum prosthesis volume, particularly in important regions such as the proximal medial region and distal lateral region) but for the fact that the positioning and orienting of the prosthesis will be found to give rise to an overlap of the prosthesis and canal image. This corresponds to physical interference of the corresponding physical objects. Accordingly, it is necessary to modify the prosthesis image, by removing material from it, to prevent interference between the prosthesis and the canal at the defined prosthesis position and orientation. This is now accomplished in such a manner as to define a minimum interference volume for removal.

To begin with, the prosthesis image is divided into segments carrying various "weights" in accordance with their relative importance. Thus, as noted previously, in the case of a hip prosthesis, it is desirable to have maximal surface contact area (and thus volume) in the proximal medial and distal lateral regions for load transmittal purposes. Thus, these regions are weighted most heavily. The determination of the volume to be removed is then begun by establishing a line joining the proximal point of intersection with the distal reference point (hereinafter referred to as the "volume-removal axis") and a "volume-removal" vector is then defined to lie at a selected orientation with respect to this axis. The orientation is preferably within the range of from a few degrees to a few tens of degrees at most. Advantageously, it is of the order of five degrees.

The volume removal vector is then rotated about the volume-removal axis to define a cone of rotation about this axis. The interfering volumes between the prosthesis and the canal are then calculated when the prosthesis is positioned in a number of preferably equally spaced, angular increments about the periphery of this cone. For example, the volume interferences may be calculated for locations every thirty degrees around the cone. The prosthesis image is now redefined by removing from the prosthesis image the volume corresponding to the minimum volume so determined. This will assure clearance between the prosthesis and the canal at the given stage of removal of the prosthesis.

Alternatively, the volume removal calculations may be repeated at successively smaller angular increments within the region of the minimum volume removal in order to further reduce the volume required to be removed to establish clearance between the prosthesis and the canal. In particular, after the initial minimum interference volume has been determined, the volume removal vector may be repositioned at the position in which the minimum volume removal was determined and a second calculation of the minimum volume undertaken by moving the volume removal vector around the first minimal point in smaller increments of arc. This can be accomplished by moving the second vector along the same path as the first vector but at smaller angular increments (e.g., at increments of 2° instead of increments of 30° as with the first vector) or can be accomplished by moving the second vector over a conical surface surrounding the first vector and having its apex coincident with the apex of the conical surface swept out by the first vector (that is, the two vectors intersect at the distal reference point). This should result in a volume removal that is smaller than the volume removal established by the first volume-removal calculation and thus represents a more nearly optimal volume-removal definition. The calculations could be repeated at even a further level of refinement but it is believed that this will not generally be necessary.

Thereafter, the prosthesis is again moved outwardly of the canal to the next cross section and the volume-removal determination repeated. This is continued until the prosthesis is removed to a level where the clinician has determined from prior experience that further volume removal is unnecessary or until movement of the prosthesis through a predetermined number of levels (e.g., three) has been accomplished without further volume removal.

The method described herein is expected to offer significant advantages over prior methods of prosthesis design. Specifically, a prosthesis designed by this method is expected to accomodate itself more closely to the internal contour of the canal in which it is implanted and thus provide a volume which more closely accomodates the canal and which minimizes the amount of artificial (e.g. cement) or natural (e.g., fibrous tissue or bone) interface material which must be utilized to interface between the prosthesis and the interior canal walls. It is believed that this will significantly reduce the incidence of failure of the interface material, and thus lead to enhanced prosthesis useful life. Further, the enlarged surface area of the prosthesis, and its closer fit to the canal, is expected to better transfer forces between prosthesis and the canal and thus minimize stress both on the canal and prosthesis themselves, as well as on the interface material. This also is expected to enhance the life of the implant.

The method of the present invention particularly accomodates itself to calculation by high speed computers. However, they are a preferred convenience, and not a required necessity, for practicing the invention.

DETAILED DESCRIPTION OF THE INVENTION

The foregoing and other and further objects and features of the invention will be more readily understood by reference to the following detailed description of the invention, when taken in conjunction with the accompanying drawings, in which.

Figure 1:
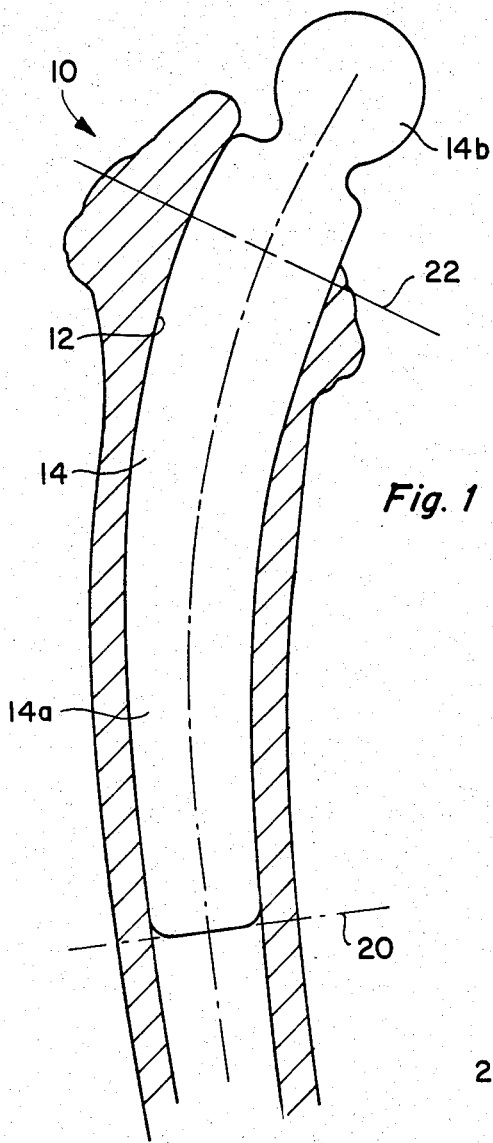
FIG. 1 is a vertical cross section of a portion of a hip showing the femoral canal and a prosthesis inserted in it at the start of the prosthesis definition operations.

In FIG. 1, a femur 10 has a hollow interior canal 12 into which is fitted a prosthesis 14 of a solid, durable metal or the like. The canal 12 may be defined by any of a number of well known techniques, such as by computer aided tomography, among others. The three-dimensional "image" of the canal is stored in any manner that is convenient for performing the operations described herein. For example, it could be stored in the form of hard-copy printouts of successive cross-sections of the canal, among other methods of storage. Advantageously, however, it is stored in the form of data points within a digital data processor or computer.

Figure 2:
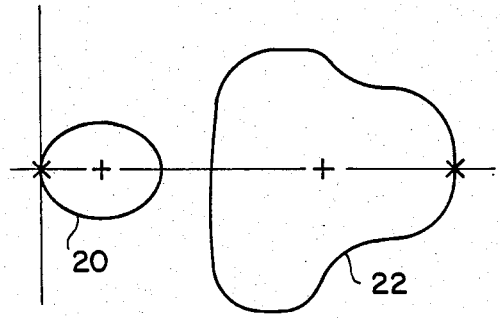
FIG. 2 is a planar projection of the base and exit cross sections of the canal of FIG. 1 showing the centroids interconnected by their centroidal line.

The prosthesis 14 has a shank 14a which fits into the femoral canal, and a head 14b which is fitted to the hip. The prosthesis is shown in its starting position in FIG. 1 prior to the time that the detailed fitting process has begun. In the starting position, the shank portion 14a is made to conform to the interior of the femoral canal. This is the ideal shape for the prosthesis in the sense of providing for maximum stress transfer from the canal bone to the prosthesis, but is not a feasible shape because of the varying cross section of the femoral canal which limits the shape of the prosthesis by the requirement that the prosthesis be removable from, and insertable into, the canal without interference with the canal shape. This is shown graphically in FIG. 2 which illustrates the projection into a common plane of typical lower and upper cross-sections of the canal. Accordingly, it is necessary to trim the starting shape of the prosthesis in order to insert it into the femoral canal.

Figure 3:
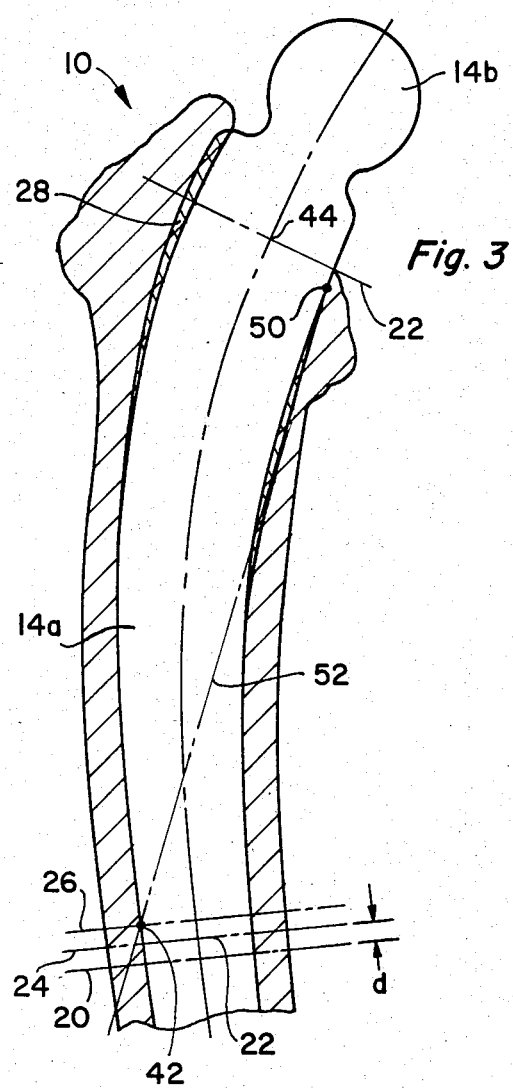
FIG. 3 is a cross section of the femoral canal and prosthesis showing the determination of the axis for location of the conical interference vector.

Turning now to FIG. 3, the shape definition process is begun by elevating the prosthesis by a predetermined amount "d" toward the upper end of the canal. This brings the base plane 22 of the prosthesis to a first level 24 within the canal. The spacing between these levels is preferably on the order of a few percent of the length of the prosthesis so as to provide a relatively smooth contour definition for the prosthesis, while not unduly magnifying the requisite calculations.

Elevating the prosthesis in this manner moves the prosthesis image from contact with the canal image (e.g., at the lower portion of the prosthesis), and causes it to overlap the canal image at other portions (e.g., at the upper portion 26 in FIG. 3). Accordingly, it is necessary to reposition the prosthesis within the canal in order to establish the location and amount of material that must be removed from it in order to allow this movement of the prosthesis. To make this determination, the distal tip of the prosthesis is moved back into contact with the femoral canal. In accordance with the present invention, the movement is accomplished in a preferred direction which is established by determining a canal reference point at the level to which the prosthesis has been moved (in FIG. 3, the level 24) and moving a reference point on the prosthesis toward the canal reference point at that level. Further in accordance with the present invention, the prosthesis reference point is established as the centroid of the base cross-section 22 of the prosthesis, while the canal reference point is determined from the centroid of the canal cross-section at the level to which the prosthesis has been moved, as well as the adjacent upper and lower canal cross sections surrounding the cross section in question.

Figure 4:
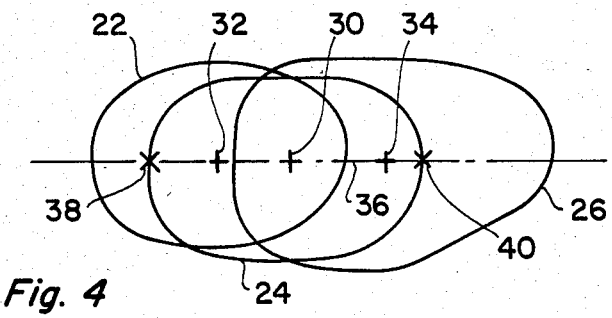
FIG. 4 shows the projection onto a common plane of selected canal cross section and the cross section of the immediately adjacent sections, illustrating definition of the canal reference points.

Specifically, and referring to FIG. 4, the cross section 24 of the canal at the level in question is shown projected onto a common plane together with the adjacent upper and lower canal cross sections 22, 26, respectively. The centroids 30, 32, 34 of these cross sections determine a centroidal line 36 joining these cross sections. This line intersects the canal reference cross section at a distal lateral intersection point 38 and a distal medial intersection point 40, respectively. Because of the curvature of the canal, the prosthesis is most readily inserted into, or removed from, the canal by moving the distal tip along the lateral canal wall, and then move the upper section of the prosthesis shank along the medial section of the canal wall. Accordingly, the lateral intersection point 38 is utilized as the reference point for repositioning the distal tip of the prosthesis. When a similar determination of a reference point is made for the upper portion of the prosthesis as described subsequently, the medial intersection point will be utilized as the reference point for the reasons just described.

Once the reference canal reference point has been determined, the base centroid 22 of the prosthesis is translated toward the canal reference until the prosthesis image coincides with the canal image at any point. The translation of the prosthesis toward the canal wall is stopped when contact is first obtained. The resultant contact point, illustratively shown as point 42 in FIG. 3, is then used as a pivot point for motion of the upper portion of the prosthesis to establish the point of contact between the upper portion and the corresponding canal cross section.

Specifically, a reference point is established for the upper or "exit" canal cross section 22 in the same manner as the reference point was defined for the lower canal cross section 24. The centroid 44 of the prosthesis coincident with the canal cross section 22 is then moved toward the upper reference point until an upper medial contact point 50 is established by contact between the prosthesis cross section and the canal cross section. Note that, as was the case with the lower contact point 42, the upper contact point 50 need not necessarily be located in the plane of the cross section in which the prosthesis centroid is being moved.

Figure 5:
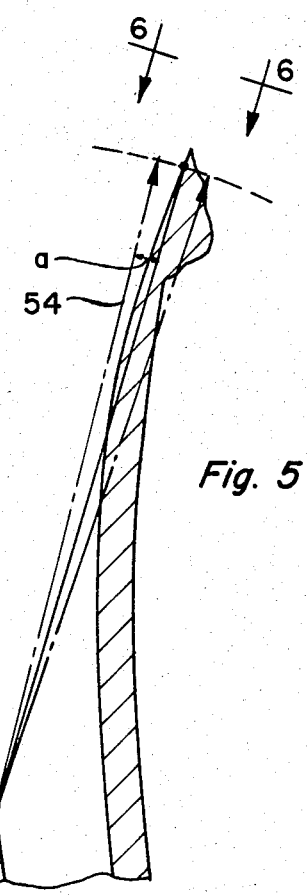
FIG. 5 is a diagrammatic view of a portion of the femur showing rotation of the interference vector and determination of overlapping or interfering volumes.

An axis 52 is now drawn between the upper and lower contact points 42, 50, respectively and a "volume-removal" vector 54 (see FIG. 5) is established at an angle "a" to the axis 52. This angle is preferably of the order of a few degrees or so, e.g., 50. The volume-removal vector is used to determine the location of the minimum volume to be removed in order to allow the prosthesis to be readily removed from the canal or inserted into it. This is accomplished by moving the vector 54 around the axis 52, while maintaining the lower contact point 42 fixed, to form an effective conical volume. The contact point on the prosthesis is located on the tip of this vector and thus this point, and the prosthesis with it, effectively is moved about with respect to the canal to seek the region in which the minimum volume required to eliminate interference is located. The extent of the overlap of the successive positions of the prosthesis with the canal as the contact pont 50 (and thus the rest of the prosthesis) is moved with this vector throughout this volume defines the interference at each position of the vector.

Figure 6:
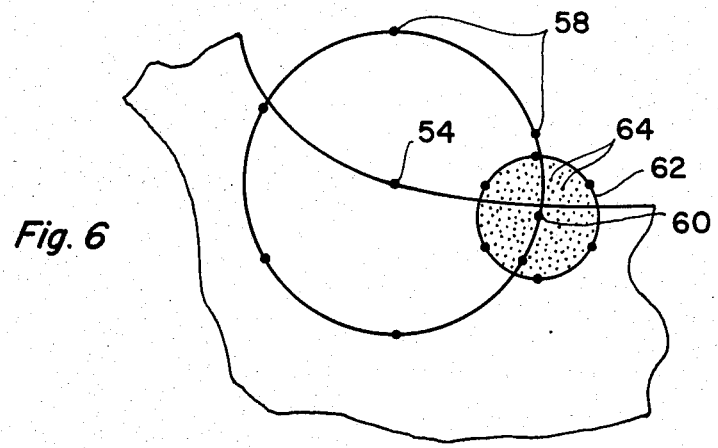
FIG. 6 is a partial view along the lines 6—6 of FIG. 5 illustrating various paths for motion of the tips of the interference vectors in defining the interference volume to be removed.

As illustrated in FIG. 6, a predetermined number of positions (indicated by points 58 in FIG. 6) on this conical surface are selected as positions for which calculations are made. For example, in FIG. 6, there are eight positions 58, spaced 45° apart, for which volume interference calculations are made. The results of these calculations are then stored, and the minimum volume is determined after the set of calculations is complete. This minimum volume is then "removed" from the prosthesis image by redefining the image to exclude this volume. When this is done, the prosthesis image is once again free of interference with the canal at the given level and thus the prosthesis can be removed from the canal to at least that level without interference with the canal surface. This process is then repeated for each of a number of displacements of the prosthesis until a point is reached at which further volume removals become unnecessary. This point can be determined a priori by the clinician, or may be determined as being that point at which a certain number of volume calculations at successive levels yield no further volume to be removed.

The calculations so far described should provide a good definition of the minimum volume to be removed. However, this can be further refined by repeating the volume removal calculation for each step. The repetition is performed in the vicinity of the region which has first been established as the minimum, but with a much finer gradation. Further, it may be accomplished by moving the volume-interference vector 54 about the same conical surface as previously, but with much smaller increments and immediately surrounding the position 59 at which the minimum has been established. Preferably, however, the repeated calculation takes the form of establishing a second volume removal vector having its remote tip coincident with the tip of the first volume removal vector and itself defining a cone of revolution about the axis from the distal contact point to the point of minimum interference volume. This is also shown illustratively in FIG. 6 as the cone 62 centered about the minimum volume interference point 60. In this calculation, the vector is moved not only about the periphery of the cone 62, but also about its interior, as indicated by points 64 in FIG. 6, to thereby establish with greater precision the optimal location of a minimum interference position.

A simplified method of determining the minimum volume of interference may be utilized when the body canal to which the prosthesis is to be fitted has a relatively limited degree of curvature, or when it is otherwise desired to reduce the requisite calculations at the possible expense of somewhat lesser control of the fit. In such situations, the trial image of the prosthesis conforming to the body canal is formed in the manner previously described. Thereafter, the prosthesis is moved upwardly by a finite amount as was previously the case, and it is translated into contact with the canal wall. The direction in which the translation is to occur may be specified a priori (for example, in the case of a hip prothesis, the lateral or the posterior directions would be preferred choices) or may be chosen in accordance with a simplified test which does not involve the calculation of centroids or centroid intersections. For example, the lower portion of the prosthesis might be moved in the direction of the closest point of the canal wall.

Next, lower and upper reference points are established for the definition of the volume removal vector. For example, the lower reference point may comprise the lower prosthesis contact point as just determined, or may comprise the centroid of the prosthesis, or may comprise a point selected by the clinician. An upper reference point adjacent the exit plane is also determined. Again, this point advantageously comprises the centroid of the prosthesis cross section in the exit plane of the canal, but may be some other point established by the clinician. These two reference points then define an axis for the volume removal vector.

As was previously the case, the volume removal vector is defined with one end (the lower end) coincident with the first reference point, and the upper end (the tip) coincident with the second reference point. The vector tip (and the prosthesis point coincident with this tip) is then displaced from the reference axis by a small angular amount (e.g., several degrees) and the vector tip (and thus the prosthesis with it) is rotated about the axis to effectively form a cone having its apex at the lower reference point. At selected angular locations about the periphery traced out by the vector tip, the interference between the prosthesis and the body portion in which it is located are calculated. The minimum one of these interference volumes is then determined, and this is removed from the prosthesis to redefine the prosthesis shape. Second and subsequent rotations and redeterminations of the minimum volume may also be determined as previously described. The prosthesis is then moved outwardly of the body structure by another increment, and the process calculations of the minimum volume repeated for this level, until the prosthesis is freely removable from the canal.

CONCLUSION

From the foregoing, it will seen that I have described a unique and systematic method of fitting a prosthesis to a body structure which is to encompass it such that the maximum volume of the prosthesis, and thus maximum surface area, is preserved, while allowing insertion and removal of the prosthesis with respect to the body structure. This is expected to lead to better fitting, and therefore more comfortable prostheses, as well as prostheses having enhanced strength and longevity within the body section. The method is particularly adapted to utilization of resources presently available, but it is not restricted to the use of any specific apparatus for obtaining or manipulating the requisite data.

Having illustrated and described my invention I claim:

1. The method of fitting a prosthesis to a body canal which is to encompass it, comprising the steps of:
   A. forming a computer image of the canal,
   B. forming a computer trial image of the prosthesis conforming to the canal
   C. establishing a distal reference point on the prosthesis,
   D. moving the prosthesis outwardly of said canal to a first level,
   E. forming a canal reference point for said level, F. translating the prosthesis distal reference point towards said canal reference point until contact is established between the prosthesis image and the canal reference point to thereby define a distal contact point, G. rotating the prosthesis image with respect to said contact point until a proximal portion of the prosthesis contacts said canal to thereby define a proximal contact point, H. establishing a rotation axis joining the distal and proximal canal contact points, and a rotation vector joining the distal canal contact point and the proximal prosthesis contact point, I. rotating said vector about said axis and determining, for each of a plurality of angular orientations of said vector about said axis, the interference volume between said prosthesis and said canal, J. redefining the prosthesis image by removing therefrom the minimum interference volume determined during the vector rotation, and K. repeating steps E through J until at least a defined amount of the prosthesis image has been removed from said canal.

2. The method of claim 1 in which weighting factors are assigned to said prosthesis throughout at least a portion of the volume thereof and in which the weighting factors are used in establishing the minimum volume to be removed from the prosthesis.

3. The method of claim 1 in which the step of defining the distal contact point includes the steps of:
(1) establishing a preferred direction for translation of the distal reference point, and
(2) translating said point in said direction.

4. The method of claim 1 in which the step of establishing a distal reference point comprises the step of establishing said reference point coincident with the centroid of the prosthesis and in which the step of defining said distal contact point includes the steps of
(1) establishing a preferred direction for translation of the distal reference point, and
(2) translating said point in said direction.

5. The method of claim 4 in which the preferred direction is established by defining a canal reference point comprising the intersection with the canal image of the planar projections of a line defined by the centroids of said canal at a plurality of longitudinally spaced locations including the centroid of the given level, as well as those adjacent to that level.

6. The method of claim 5 in which the prosthesis base centroid is brought to a position substantially coincident with the canal cross section centroid at a given level prior to translation toward said distal reference point.

7. The method of claim 1 in which said prosthesis is removed from said canal at each step substantially along a line joining the centroids of the canal cross-sections at the levels through which the prosthesis is moved.

8. The method of claim 1 which includes the further step of rotating said vector through each of a plurality of angular orientations of diminished angular separation in the region of the minimum interference volume defined by the prior set of rotations and establishing the minimum interference volume therefrom to thereby define an enhanced minimum interference volume for use in redefining the prosthesis image.

9. The method of fitting a prosthesis to a body canal which is to encompass it, comprising the steps of:
A. forming a longitudinal computer image of the canal interior, B. calculating the centroid of a base prosthesis cross-section at a distal end thereof, C. calculating the centroids of a plurality of longitudinally-spaced cross-sections of said canal between said base cross section and an exit cross-section at the proximal end of said canal, D. defining, for each canal cross-section, a reference point by calculating the intersections of a line joining a plurality of canal centroids with the contours of said canal cross-sections when said line and said cross-sections are projected onto a common plane, E. moving the computer prosthesis image longitudinally in said canal along the centroidal line of the canal to the adjacent canal cross-section and translating the base centroid of said prosthesis toward the reference point of said cross-section until the prosthesis base cross-section contacts the canal contour at a point to thereby establish an interference point, F. determining the centroid of said prosthesis at a cross-section coincident with the canal exit cross-section and rotating said centroid toward the canal exit cross-section reference point about a line through the interference contact point until the prosthesis image contacts the canal image in the vicinity of said reference point, G. rotating a vector about an axis defined by said base and exit plane interference points and determining, for each of a plurality of angular positions of said vector about said line, the volume interference between the prosthesis image and the canal image for such positions, H. determining the minimum volume interference and redefining the prosthesis image to remove said minimum volume therefrom, and I. repeating steps E through H until the prosthesis image is removeable from the canal without further interference.

10. The method of fitting a prosthesis to a body canal which is to encompass it comprising the steps
A. forming a computer image of the canal
B. forming a computer image of the prosthesis generally conforming to the canal,
C. withdrawing said prosthesis from the canal by a predetermined amount,
D. positioning one end of the prosthesis on a first contact point of a path along the canal wall along which said end is to move during withdrawal,
E. rotating the prosthesis about an axis defined by selected reference points on the upper and lower portions of said prosthesis and calculating the volume interference between the prosthesis and the canal for each of a plurality of positions about said axis,
F. selecting the minimum interference volume and redefining the prosthesis image by removal of said volume therefrom;and
G. repeating the steps of paragraph C through F until the prosthesis can be withdrawn without further interference.

11. The method of claim 10 in which the step of rotating the prosthesis includes the step of further rotating the prosthesis through a volume surrounding the position for which the minimum volume removal has been determined to thereby further redefine the minimal volume removal.

12. The method of claim 10 in which said canal wall path is defined for each canal cross-section by the intersection with said cross section with the planar projection of a line joining the centroids of surrounding canal cross sections.

13. The method of claim 12 in which the step of positioning one end of the prosthesis on said first contact point comprises the step of translating a selected reference point on a lower plane of the prosthesis toward corresponding reference point on said canal wall at the corresponding canal cross section until contact between the prosthesis and the canal wall is established.

* * * * *